(12) United States Patent
Walker

(10) Patent No.: US 6,482,175 B1
(45) Date of Patent: Nov. 19, 2002

(54) TWO-PART SURGICAL INCISION IMPLEMENT FOR FORMING AN OPENING IN THE SKIN

(75) Inventor: Justin Robert Andrew Walker, London (GB)

(73) Assignee: BTG International Limited, London (GB)

(*) Notice: Subject to any disclaimer, the term of this patent is extended or adjusted under 35 U.S.C. 154(b) by 0 days.

(21) Appl. No.: 09/421,386

(22) Filed: Oct. 20, 1999

Related U.S. Application Data

(63) Continuation of application No. PCT/GB98/01044, filed on Apr. 9, 1998.

(30) Foreign Application Priority Data

Apr. 21, 1997 (GB) .............................................. 9707997

(51) Int. Cl.⁷ ................................................ A61M 5/00
(52) U.S. Cl. .................. 604/115; 604/116; 604/165.01; 604/167.04; 604/167.06; 606/185
(58) Field of Search ............................ 606/1, 184, 185, 606/150, 153–156, 99, 108, 167, 188; 604/164, 165, 165.01, 165.03, 166.01, 167.04, 167.06, 115, 116

(56) References Cited

U.S. PATENT DOCUMENTS

| 3,656,485 A | 4/1972 | Robertson |
| 3,920,023 A | 11/1975 | Dye et al. |
| 4,617,929 A | 10/1986 | Gill |
| 4,716,901 A | * 1/1988 | Jackson et al. |
| 5,123,402 A | 6/1992 | Vandenbossche et al. |
| 5,152,749 A | * 10/1992 | Giesy et al. |
| 5,407,427 A | * 4/1995 | Zhu et al. ..................... 604/26 |
| 5,437,683 A | 8/1995 | Neumann et al. |
| 5,443,452 A | * 8/1995 | Hart et al. .................. 137/849 |
| 5,628,732 A | * 5/1997 | Antoon et al. ......... 604/167.06 |
| 5,643,227 A | * 7/1997 | Stevens .................. 604/167.02 |
| 5,720,759 A | * 2/1998 | Green et al. ........... 604/165.01 |

FOREIGN PATENT DOCUMENTS

| DK | 39 19 740 A1 | 12/1990 |
| WO | WO 85/04089 | 9/1985 |
| WO | WO 93/25264 | 12/1993 |

* cited by examiner

Primary Examiner—David J. Isabella
Assistant Examiner—Urmi Chattopadhyay
(74) Attorney, Agent, or Firm—Nixon & Vanderhye

(57) ABSTRACT

A surgical implement for forming an opening in the skin of a patient comprises two bodies: a first for application to one side of the skin and a second, having an incision element, for application to the other side of the skin to co-operate with the first body. The opening in the skin is formed simply and safely by placing the first and second bodies either side of the skin and moving the incision element.

20 Claims, 3 Drawing Sheets

TWO-PART SURGICAL INCISION IMPLEMENT FOR FORMING AN OPENING IN THE SKIN

This is a continuation of PCT application No. PCT/GB98/01044, filed Apr. 9, 1998, the entire content of which is hereby incorporated by reference in this application.

The invention concerns a surgical implement for forming an opening in the skin of a patient, in particular for use in procedures involving the introduction of drainage tubing into body cavities.

BACKGROUND OF THE INVENTION

Surgical drains are routinely inserted into body cavities during certain surgical operations in order to allow fluid communication between the interior and the exterior. To avoid wound complications it is common practice not to route such drains via the primary surgical incision, but instead through a different part of the body wall by way of a smaller secondary incision. Introduction of the surgical drain involves passage of a tube from the body cavity (such as the abdomen or the thorax) through the body wall and, as skin is generally the most resistant tissue to be traversed, the conventional method is to employ an appropriately sharp metal introducer passed from the interior to the exterior, whilst the surgeon's free hand is used to provide counterpressure on the outside of the skin. An example of such an instrument is disclosed in U.S. Pat. No. 4,716,901. Whilst quick and simple, there are a number of inherent risks with this procedure. Firstly, the introduction of a sharp instrument into a body cavity threatens injury by laceration or perforation to the patient's viscera. Secondly, because of the necessary proximity of the surgeon's hand to the point of exit of the sharp introducer, the surgeon is exposed to a significant risk of self injury, with the result of both physical trauma and, more importantly, 'drainstick' injury with the attendant risk of transmission of serious infective disease such as HIV and Hepatitis B.

Once the sharp introducer has passed through the skin the drain, which is conventionally a simple flexible latex tube attached to the rear end of the introducer, is pulled through the body wall opening. The introducer is then cut from the tube and the tube is sutured into place to prevent it being inadvertently pulled out of the body. This is generally done by stitching a suture loop to the skin, and then looping sutures around the tubing for a short distance from the skin exit point.

FIG. 1 illustrates schematically a part of the above-described conventional procedure, with the introducer 10 (attached to drain tubing 11) in the process of being pushed through the body wall 12 from the interior to the exterior, whilst the fingers 1, of the surgeon's free hand are shown applying a counterpressure to the tented outer surface of the skin.

DE-A-3919740 and U.S. Pat. No. 5,152,749 disclose devices for inserting a catheter into the bladder in which a hollow sheath element carrying a sharp incision element is introduced into the bladder via the urethra, and the incision element is moved relative to the sheath to cut an opening through the wall of the bladder and through to the exterior. A catheter introducer is then attached to the incision element and the proximal end of incision element is pulled to draw the catheter into the bladder from the exterior.

SUMMARY OF THE INVENTION

The object of the invention is to provide a surgical implement for forming an opening in the skin of a patient which overcomes at least some of the drawbacks of conventional procedures. To this end, the invention provides a surgical implement for forming an opening in the skin of a patient comprising a first body having a distal end for application to one side of the skin and a second body for application to the other side of the skin to co-operate with the first body, the second body having: a sharp skin incision element moveably mounted thereto, a hollow form adapted to receive and locate the distal end of the first body, and means for moving said incision element relative to said second body. According to an alternative aspect of the invention, there is provided a surgical implement for forming an opening in the skin of a patient comprising a first body for application to one side of the skin; a second body having a sharp skin incision element moveably mounted thereto and means for causing movement of said incision element; whereby in use the first body can be applied to one side of the skin to cause tenting of the skin in a direction towards the other side of the skin and the second body can be applied to the other side of the skin to co-operate with the first body via the skin, while protecting the surrounding skin.

Preferably, the distal end of the first body is of blunt form to minimise damage to the one side of the skin. Said first body distal end may be provided with a recess, such that said movement of the incision element carries the element into said recess.

Use of the invention reduces the risk of harm to both the patient and to medical staff in making an incision in the wall of a body cavity, for example when introducing a drain tube to the body cavity. For such an operation, the surgical implement of the invention may include a surgical drain tube attached or attachable to the proximal end of said first body.

In a preferred form, said second body is of a generally tapering form, tapering from a distal portion for contacting the skin to a proximal portion to which said incision element is mounted. An opening may be provided in the proximal portion of said second body, providing access to the hollow interior of the second body, and the incision element may be arranged to travel through said opening between a first position, when it is held outside the opening, and a second position, when it is positioned within the hollow interior of the said second body.

When the surgical implement is to be used in respect of the introduction of a surgical drain, said opening can be dimensioned to allow passage therethrough of said first body.

Preferably, the incision element is supported by at least two wall sections projecting from the exterior of said second body, such that manipulation of said wall sections causes the incision element to travel between said first position and said second position.

The incision element may be arranged to be detachable from said second body on reaching said second position, and to this end a preferred embodiment is provided with an incision element mounted to said second body by way of at least one frangible element which breaks when the incision element is in said second position.

Preferably, the incision element depends from at least two substantially planar wings which are connected to the said wall sections and which, when the incision element is in its first position, are orientated obliquely to the incision element travel direction, such that an urging together of said wall sections will cause the incision element to travel towards said second position.

Said second body may be provided with opposed barb elements, and preferably said barb elements are provided on said wall sections to allow securement of a surgical drain tube passed through said opening in the distal portion of said second body.

Additionally or alternatively, said second body is provided with suture points to assist in its securement to said other side of the skin during surgical procedure.

For drain tube introduction the invention may take the form of a surgical kit comprising at least one surgical implement according to the invention, the kit including a range of said first bodies and a range of said second bodies, the bodies in each range differing from one another in at least one characteristic.

According to a further aspect of the invention, there is provided a method of forming an opening in the skin of a patient. said method comprising:

applying a distal end of a first body to one side of the skin;

applying a second body to the other side of the skin, the second body having a hollow form adapted to receive and locate the distal end of the first body via the skin while protecting the surrounding skin area, the second body having a sharp skin incision element moveably mounted thereto; and bringing the first and the second body into mutual co-operation respectively on different sides of the skin and moving said incision element to puncture the skin.

Preferably, the method includes the step, after puncturing the skin, of passing said first body through said second body, and then passing a surgical drain tube through the skin incision and through said second body.

BRIEF DESCRIPTION OF THE DRAWINGS

The invention will now be described more fully by way of non-limiting embodiments with reference to the accompanying drawing, in which.

DETAILED DESCRIPTION OF PREFERRED EMBODIMENTS

The surgical implement of the invention comprises two mutually cooperating parts, a first body and a second body, respectively an introducer and a skin cap device.

Figure 1:
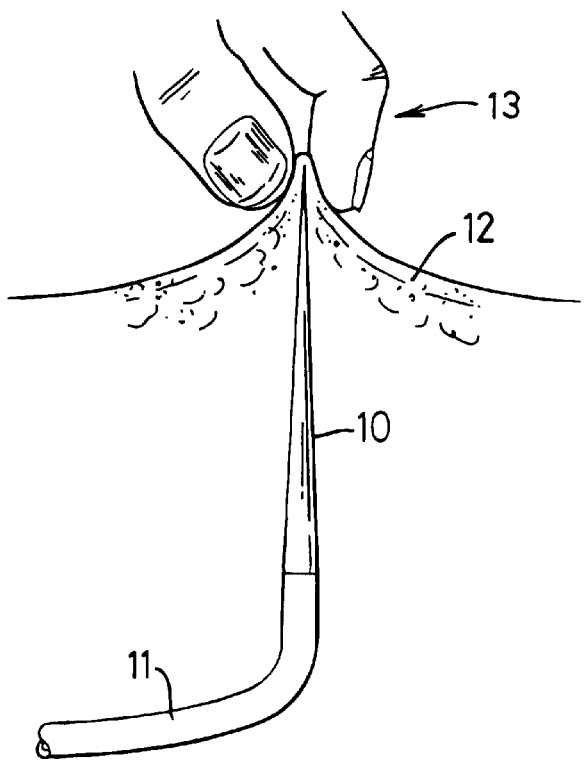
FIG. 1 illustrates the prior art procedure for forming an opening in the skin of a patient for the introduction of a drainage tube into a body cavity.
Figure 2:
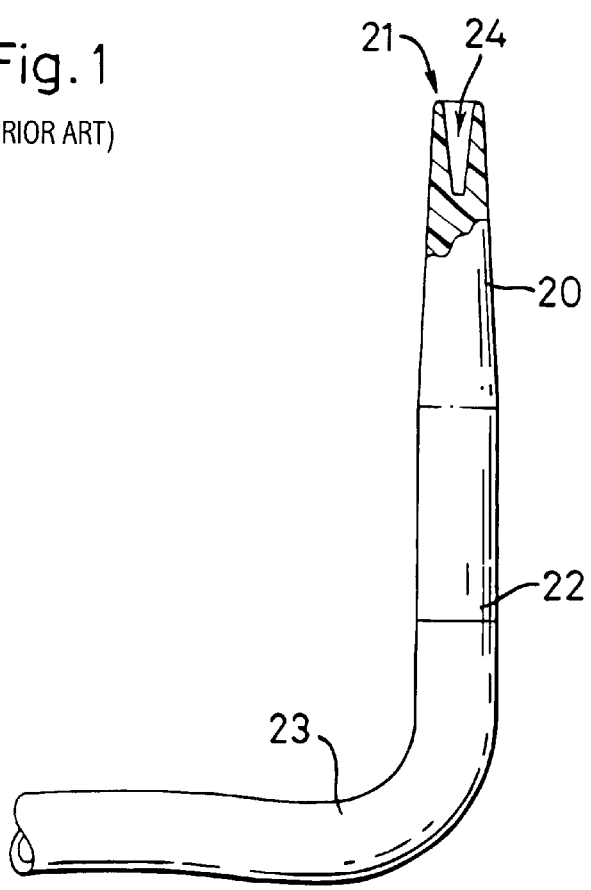
FIG. 2 illustrates an introducer of a surgical implement according to the present invention.

The introducer of FIG. 2 comprises an elongated cylindrical body 20, circular in cross section, tapering towards a blunt distal nose 21. The proximal end 22 is attached or attachable to a length of conventional drain tubing 23, whilst at its distal nose the introducer has a deep recess 24 in the form of an inverted cone. As will be explained further below, the introducer is not intended to pierce the patient's skin, but simply to be pushed firmly against the inside of the body wall in order to tent the skin outwardly. There is therefore no requirement that the introducer is made of metal, and it can instead be realised in, for example, a stiff plastic material or latex.

Figure 3:
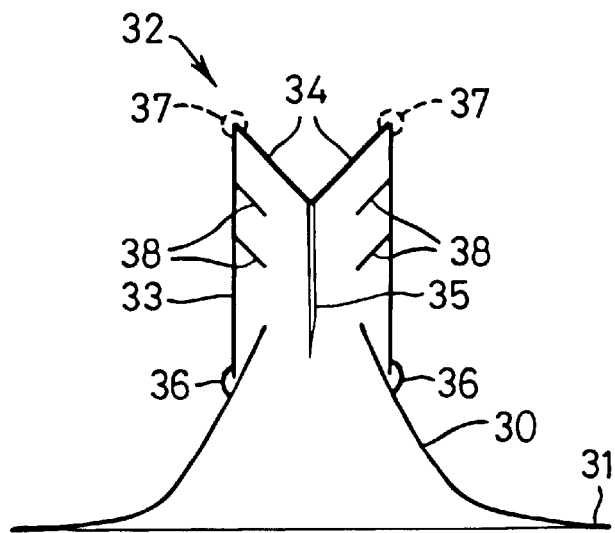
FIG. 3 illustrates in sectional view a skin cap device of the surgical implement according to the invention, for use with the introducer of FIG. 2.

The second part of the surgical implement, the skin cap device (FIG. 3), comprises a generally conical body 30 with an annular base flange 31, near the apex of which is attached a central blade-mounting means 32. The blade-mounting means consists of two upwardly projecting lateral opposed walls 33, which are generally curved towards one another when seen in plan view to surround the open apex of the conical body 30. From the central region of the upper edges of the two opposed walls are attached two downwardly and inwardly projecting planar wings 34 which meet and connect centrally and which support a downwardly-directed sharp disposable blade 35, which is so sized as to fit within the apical aperture of the conical body 30. The connections 36 between the two walls 33 and the conical body 30 and those 37 between the two walls and the wings 34 are formed as resilient hinges, which may be conveniently realised by moulding these items in a single piece from a plastics material, the inherent flexibility of the material providing the required hinges. The connection between the two planar wings 34 is also formed as a resilient hinge. The connections 37 between the two walls 33 and the wings 34 are moreover designed to be frangible under a certain force, as will be described below, and this characteristic may also be provided by an appropriate design in plastics material. On the inside faces of the two opposed walls 33 are arranged sets of downwardly and inwardly projecting barb wings 38, which extend inwardly to leave a gap therebetween approximately the same width as the diameter of the open apex of the conical body. These barb wings 36 serve to restrain the movement of the drain tube once it is in place and their function is further explained below with reference to the operation of the surgical implement.

Figure 4:
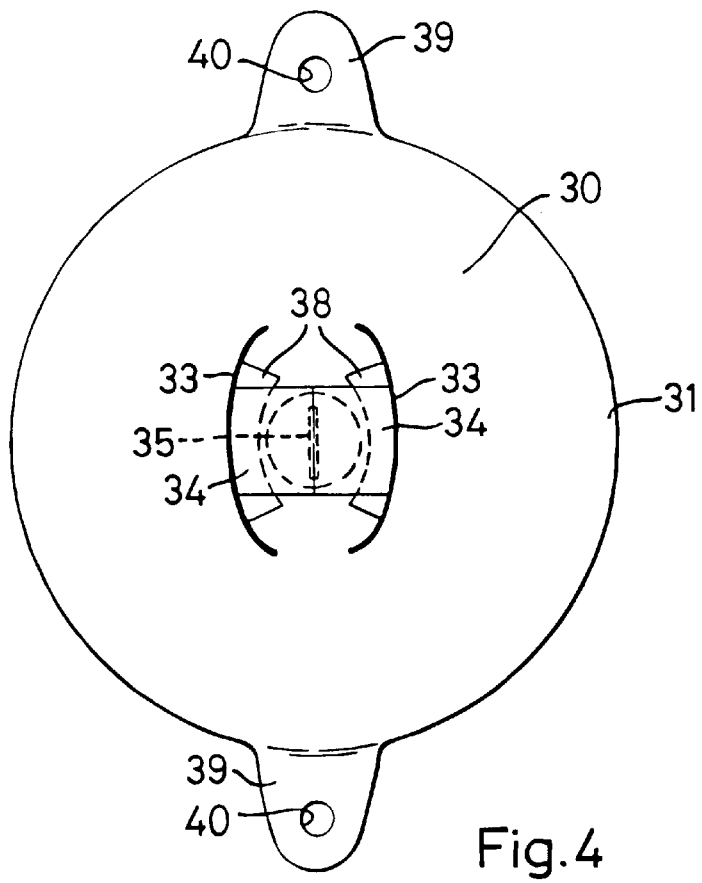
FIG. 4 shows a plan view of the skin cap device of FIG. 3.

The skin cap device is shown in plan view in FIG. 4, and the shaping and relative dimensions of the various component parts described above can be seen from this drawing. On opposed sides of the outer edge of the base flange 31 are provided two projecting lugs 39 each with a suture port 40 to enable the skin cap device to be sutured in place to the patient's skin.

Figure 5:
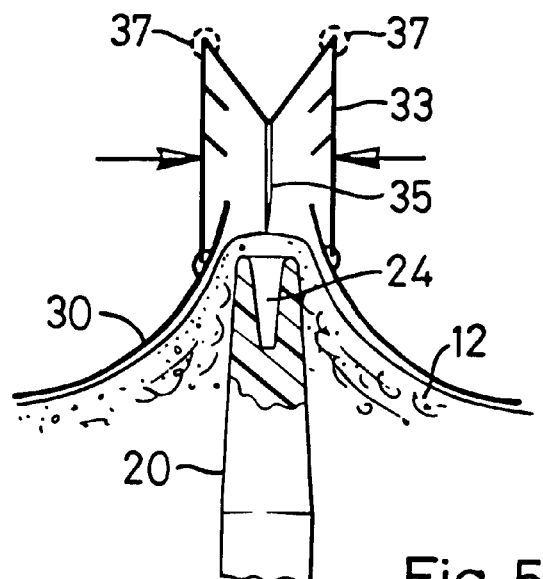
FIG. 5 shows a sectional view of the surgical implement in place and illustrates an operational procedure according to the invention.
Figure 6:
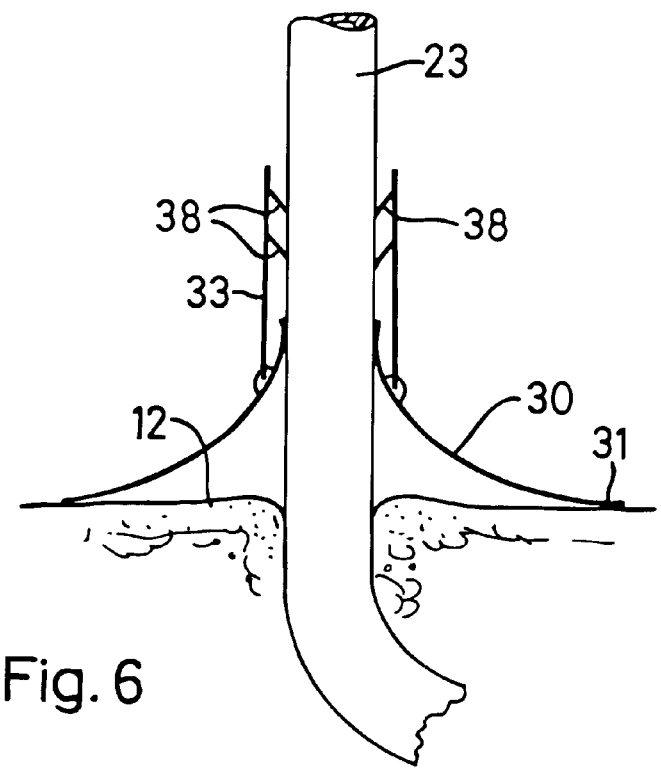
FIG. 6 shows in section the surgical implement in place once a drain tube has been pushed out through the opening in the skin and through the skin cap device.

The surgical procedure will now be described with reference to FIGS. 5 and 6 to illustrate the use of the surgical implement of the invention.

Firstly, the desired site for exit of the drain is selected and prepared by application of an topical antiseptic solution. Using the non-dominant hand, the surgeon then places the skin cap device over the desired exit site, ensuring it is placed with the blade 35 orientated in the line of election, to ensure an incision in that same line of election and therefore to minimise subsequent scarring. To aid in the correct positioning of the skin cap device, it is preferably manufactured from a transparent material and may carry marking to clearly indicate orientation. The introducer is then manipulated by the surgeon's dominant hand from within the body cavity towards the body wall on the inside of the exit site.

The blunt distal nose 21 of the introducer is then used to tent the skin outwardly within the hollow interior of the conical body 30, whilst the surgeon's fingers hold the skin cap device firmly against the skin around its base flange 31. The skin is therefore pushed up towards the apical hole of the conical body, sandwiched between the introducer and the inside periphery of the top portion of the conical body, as shown in FIG. 5.

With the surgeon's fingers still held against the base flange 31 the two walls 33 are squeezed together. The hinge connections 36 and 37 therefore provide that the wings 34 and the dependent blade 35 are driven directly downwards, the blade thus incising through the skin at the precise desired location. The blade having passed through the skin and underlying tissue layers is then received in the recess 24 of the distal nose 21 of the introducer, so minimising any risk-to the surrounding tissue. The surgeon then releases the squeezing action on the two walls 33 and, continuing to hold the skin cap device securely against the skin around the peripheral base flange 31, pushes the introducer body out through the newly-formed opening in the skin. This action serves to snap the wings 34 from the lateral walls 33 at the frangible connections 37, and the blade with the wings still attached remains safely concealed within the recess 24.

The introducer is pulled through the conical body 30 of the skin cap device until the appendant drain tube 23 emerges. This is then pulled to length and the surgeon then once again squeezes the two lateral walls 33 together to push the barb wings 38 against the outside surface of the tube. These barb wings serve to prevent the tube from inadvertently being pulled further out of the patient's body, and may be then held in this securing position by means of, for example, a length of inelastic tape around the external surface of the lateral walls 33.

Finally, the projecting lugs 39 of the conical body 30 are securely sutured to the skin by way of the suture ports 40.

The surgical implement of the invention thus ensures minimum risk of harm to both the patient and medical staff in the procedure of introducing the drain tube. Before use, the sharp edge of the blade is, by design, concealed in the interior of the skin cap device and so is highly unlikely to cause any accidental damage before use. Once the blade has been used to cut through the skin it is wholly concealed within the recess of the nose of the introducer, and said recess may be provided with a suitable arrangement for retaining the blade. For example, it may be designed to be slightly shorter than the depth to which the blade is to be driven to ensure the latter is embedded into the material of the introducer and is thus wholly captive therein. The skin cap device not only provides a simple way of accurately operating the incision blade with just two fingers of one hand, whilst fully protecting the fingers and the surrounding skin of the patient, but also doubles as a convenient and simple securing mechanism for the drain tubing, avoiding the need to attempt the conventional, somewhat unsatisfactory, direct suturing of the tube to the skin. Furthermore, by leaving the skin cap device in place, a relatively sterile zone is provided around the incision site, so helping to reduce the risk of microorganisms reaching the wound and tracking along the drain tube into the patient.

As mentioned above, both the introducer and the skin cap device are preferably fabricated from a semi-rigid plastics or latex material, with the flat metal blade mounted to the projecting wings 34 of the skin cap device. Both parts of the surgical implement are preferably provided as sterile disposable items, which may be packaged together or as separately selectable items, and are ideally designed for low cost mass production.

Clearly, the invention has application to a number of different types of surgical procedure, and the precise dimensions and characteristics of the surgical implement may be varied as appropriate to the particular application. For example, drain tubes might typically be required in the abdominal cavity during a laparotomy for peritonitis. In intestinal anastomoses, in plastic surgery and vascular surgery, and in surgical procedures in the field of obstetrics and gynaecology, such drains are also commonly employed.

The blade of the surgical implement might typically be of about 5 mm in length to make an incision which will accommodate a standard diameter of drain tubing, and the skin cap device might be a few centimetres in total diameter, being taller and wider for thicker or fatter skin types. The blade may alternatively be replaced by any other suitable incision element, such as an appropriately sized needle.

In addition to its use in conventional surgery, the surgical implement of the invention may find application in so-called 'keyhole surgery'. In such procedures, the surgeon makes a first small opening in the skin from outside and then conventionally proceeds to make the additional access openings from outside the body. The invention may be employed by making use of an elongated introducer of arcuate form in combination with a skin cap device as hitherto described to form the second and subsequent openings, thus reducing the risk of inadvertently damaging the patient's viscera. An endoscopic instrument or attachment may be used to assist in guiding the introducer within the body.

It is to be noted in this description and the accompanying claims that the terms 'distal' and 'proximal' are used in a conventional sense, ie. with reference to the surgeon. For the introducer, therefore, the distal part is the part to be applied to the inner wall of the body cavity, and for the skin cap device the distal part is that part to be applied to the skin.

What is claimed is:

1. A two-part surgical incision implement for forming an opening in the skin of a patient comprising:
    a first body having a rigid or semi-rigid distal end for application to one side of the skin to create an area of tented skin; and
    a second body, separate from the first, for application to the other side of the tented area of skin to co-operate with the first body, the second body having:
    a hollow form for locating and receiving the distal end of the first body via the patient's skin, and
    an integral sharp skin incision element moveably mounted thereto.

2. A two-part surgical incision implement according to claim 1 wherein the distal end of the first body is of blunt form to minimise damage to the one side of the skin.

3. A two-part surgical incision implement according to claim 1 wherein the distal end of said first body is provided with a recess, such that said movement of the incision element carries the incision element into said recess.

4. A two-part surgical incision implement according to claim 1 including a surgical drain tube attached to the proximal end of said first body.

5. A two-part surgical incision implement claim 1, wherein said second body is of a generally tapering form, tapering from a distal portion for contacting the skin to a proximal portion to which said incision element is mounted.

6. A two-part surgical incision implement according to claim 1, wherein an opening is provided in the distal portion of said second body, providing access to the hollow interior of the second body, and the incision element is arranged to travel through said opening between a first position, when it is held outside the opening, and a second position, when it is positioned within the hollow interior of the said second body.

7. A two-part surgical incision implement according to claim 6, wherein said opening is dimensioned to allow passage therethrough of said first body.

8. A two-part surgical incision implement according to claim 7, wherein the incision element depends from at least two substantially planar wings which are connected to the said wall sections and which, when the incision element is in its first position, are orientated obliquely to the incision element travel direction, such that an urging together of said wall sections will cause the incision element to travel towards said second position.

9. A two-part surgical incision implement according to claim 7 wherein the incision element is supported by at least two wall sections projecting inwardly from the interior portion of said second body, such that manipulation of said wall sections causes the incision element to travel between said first position and said seconds position.

10. A two-part surgical incision implement according to claim 7, to wherein said incision element is detachable from said second body on reaching said second position.

11. A two-part surgical incision implement according to claim 10, wherein said incision element is mounted to said second body by way of at least one frangible element which breaks when the incision element is in said second position.

12. A two-part surgical incision implement according to claim 1 wherein said second body is provided with opposed barb elements.

13. A two-part surgical incision implement according to claim 12 wherein said barb elements are provided on wall sections to secure a surgical drain tube past through said opening in the distal portion of said second body.

14. A two-part surgical incision implement according to claim 1, wherein said second body is provided with suture points to assist in securement of said second body to said other side of the skin during surgical procedure.

15. A two-part surgical incision implement according to claim 1, wherein said second body is fabricated at least partly from transparent material.

16. A surgical kit for drain tube introduction comprising two or more two-part surgical incision implements according to claim 1, said implements including a plurality of said first and second bodies, the bodies differing from one another in at least one of shape and size.

17. A two-part surgical incision implement according to claim 1 including a surgical drain tube attachable to the proximal end of said first body.

18. A two-part surgical incision implement for forming an opening in the skin of a patient comprising:
 a first body for application to one side of the skin; and
 a second body having an integral sharp skin incision element moveably mounted thereto via wall sections projecting from the second body, whereby in use the first body can be applied to one side of the skin to cause tenting of the skin in a direction towards the other side of the skin and the second body can be applied to the other side of the skin to co-operate with the first body via the skin, while protecting the surrounding skin; such that upon manipulation of said wall sections said incision element can move relative to the skin held between the first body and the second body to puncture the skin.

19. A surgical implement for forming an opening in the skin of a patient comprising:
 a hollow body having distal and proximal openings;
 a sharp incision element mounted movably to said hollow body and detachable from said body; and
 restraining elements located within said hollow body for restraining a drain tube when passed through said body;
 said hollow body being adapted when said incision element is detached to have a surgical drain tube passed through said body.

20. A surgical implement for forming an opening in the skin of a patient comprising:
 a hollow body having a longitudinal axis and flexible walls; and
 a sharp incision element mounted within said hollow body and being detachable therefrom, said incision element being movable in a direction parallel to said longitudinal axis when said flexible walls are compressed in a direction transverse to said longitudinal axis;
 said hollow body being adapted when said incision element is detached to have a surgical drain tube passed through said body.

* * * * *